(12) United States Patent
Kaul

(10) Patent No.: US 8,206,295 B2
(45) Date of Patent: Jun. 26, 2012

(54) SUCTION-BASED TISSUE MANIPULATOR

(76) Inventor: Ashutosh Kaul, Scarsdale, NY (US)

( * ) Notice: Subject to any disclaimer, the term of this patent is extended or adjusted under 35 U.S.C. 154(b) by 207 days.

(21) Appl. No.: 12/484,287

(22) Filed: Jun. 15, 2009

(65) Prior Publication Data

US 2010/0317926 A1 Dec. 16, 2010

(51) Int. Cl.
*A61B 1/32* (2006.01)
(52) U.S. Cl. .......... 600/210; 604/313
(58) Field of Classification Search .......... 600/201, 600/210, 206, 207, 214; 604/289, 290, 312, 604/313, 128, 451
See application file for complete search history.

(56) References Cited

U.S. PATENT DOCUMENTS

| | | | |
|---|---|---|---|
| 5,201,752 A | 4/1993 | Brown et al. | |
| 5,415,160 A * | 5/1995 | Ortiz et al. | 600/230 |
| 5,450,842 A | 9/1995 | Tovey et al. | |
| 5,545,123 A * | 8/1996 | Ortiz et al. | 600/235 |
| 5,562,603 A | 10/1996 | Moll et al. | |
| 5,643,229 A | 7/1997 | Sinaiko | |
| 5,885,271 A * | 3/1999 | Hamilton et al. | 606/1 |
| 5,944,736 A | 8/1999 | Taylor et al. | |
| 5,954,638 A | 9/1999 | Spranza, III | |
| 6,090,041 A | 7/2000 | Clark et al. | |
| 6,241,658 B1 | 6/2001 | Goodrich | |
| 6,394,948 B1 * | 5/2002 | Borst et al. | 600/37 |
| 6,641,575 B1 * | 11/2003 | Lonky | 604/540 |
| 6,988,984 B2 * | 1/2006 | Parsons et al. | 600/37 |
| 7,179,224 B2 | 2/2007 | Willis | |

(Continued)

FOREIGN PATENT DOCUMENTS

AU 2003291306 6/2004

OTHER PUBLICATIONS

A New Device With Pressure Regulation for Microsurgical Suction; Technical Note, Sebastio Gusmao, Science Direct, Surgical Neurology, vol. 63, Supplement 1 , pp. S36-S38 (Jan. 2005).

*Primary Examiner* — Eduardo C Robert
*Assistant Examiner* — Stuart S Bray
(74) *Attorney, Agent, or Firm* — Gordon & Jacobson, PC

(57) ABSTRACT

A surgical assembly including a flexible shell that defines a flexible sheet-like structure with a major top wall opposite a major bottom wall. The top wall is impermeable to air flow therethrough and has a first set of holes that allow for air flow therethrough. The bottom wall is impermeable to air flow therethrough and has a second set of holes that allow for air flow therethrough. A first fluid path supplies a source of suction to the first set of holes in a manner that is independent to suction supplied the second set of holes. A second fluid path supplies a source of suction to the second set of holes in a manner that is independent to suction supplied to the first set of holes. The supply of suction to the first set of holes is used to engage and hold tissue adjacent the top wall by suction forces applied through the first set of holes. The supply of suction to the second set of holes is used to engage and hold tissue adjacent the bottom wall by suction forces applied through the second set of holes. The tissue that is engaged adjacent the top wall is sealably disposed about the first set of holes, and tissue that is engaged adjacent the bottom wall is sealably disposed about the second set of holes.

17 Claims, 6 Drawing Sheets

U.S. PATENT DOCUMENTS

| | | |
|---|---|---|
| 7,326,177 B2 | 2/2008 | Williamson, IV et al. |
| 7,766,817 B2 * | 8/2010 | Peng et al. .................. 600/37 |
| 7,846,141 B2 * | 12/2010 | Weston ...................... 604/313 |
| 7,867,206 B2 * | 1/2011 | Lockwood et al. .......... 604/313 |
| 7,931,579 B2 * | 4/2011 | Bertolero et al. ............. 600/37 |
| 2002/0082470 A1 * | 6/2002 | DeVries et al. ............... 600/37 |
| 2004/0267303 A1 * | 12/2004 | Guenst ....................... 606/205 |
| 2005/0010197 A1 | 1/2005 | Lau et al. |
| 2005/0171403 A1 | 8/2005 | Paolitto et al. |
| 2006/0041194 A1 * | 2/2006 | Sorochkin et al. ........... 600/201 |
| 2006/0200002 A1 * | 9/2006 | Guenst ....................... 600/201 |
| 2007/0179343 A1 | 8/2007 | Shelokov |
| 2007/0238917 A1 | 10/2007 | Peng et al. |
| 2008/0091078 A1 | 4/2008 | Roth et al. |
| 2009/0137984 A1 * | 5/2009 | Minnelli ..................... 604/540 |
| 2009/0287060 A1 * | 11/2009 | Pell et al. .................... 600/201 |

* cited by examiner

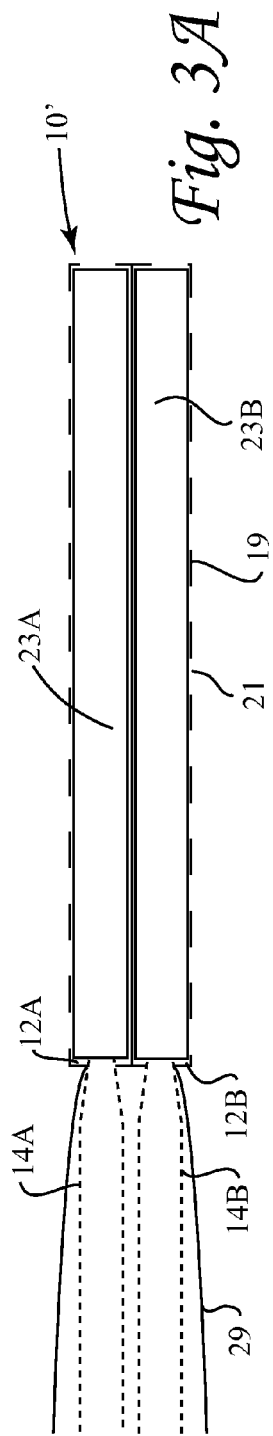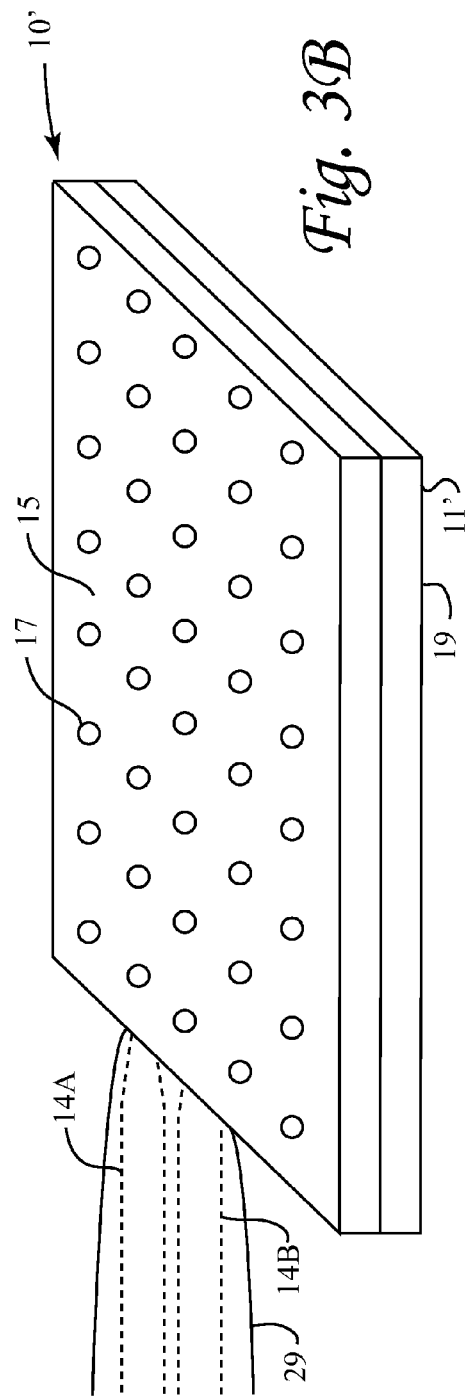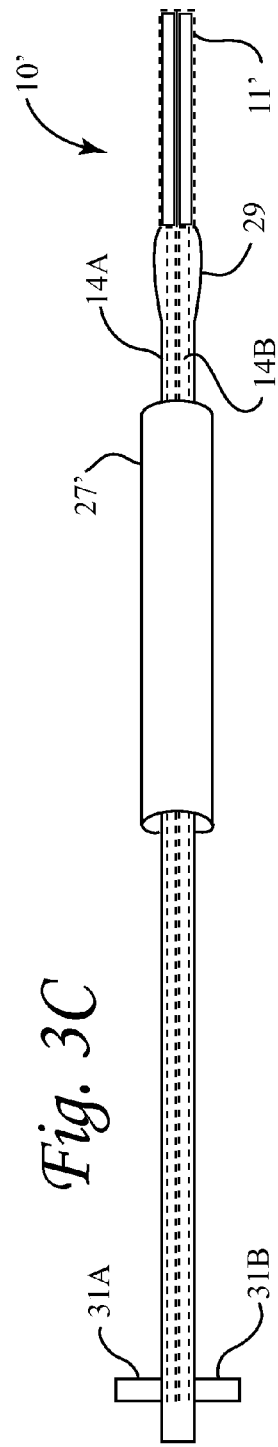

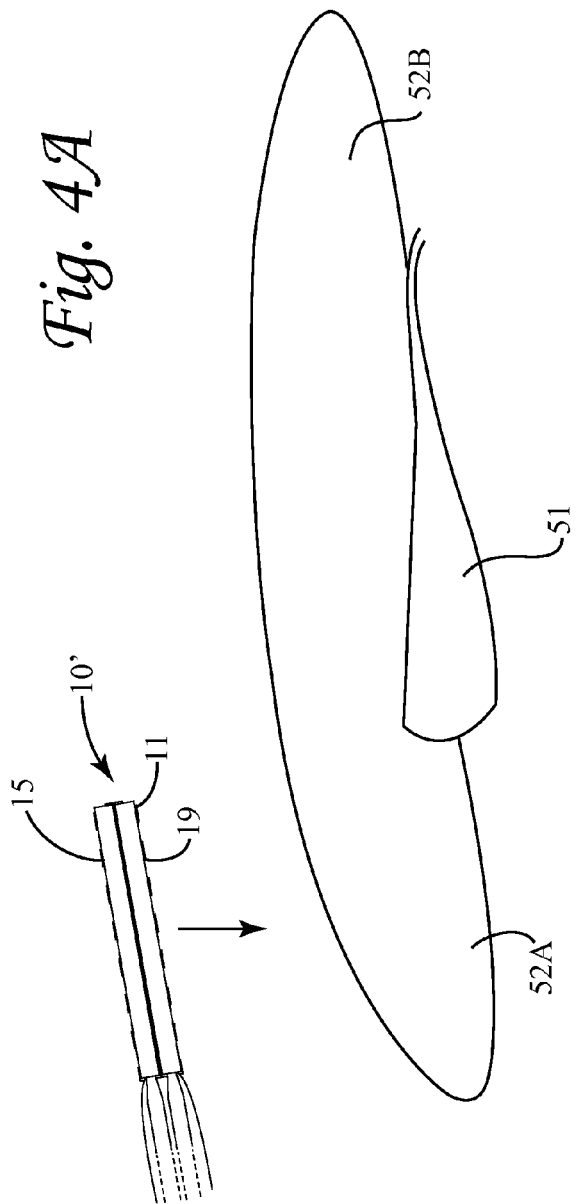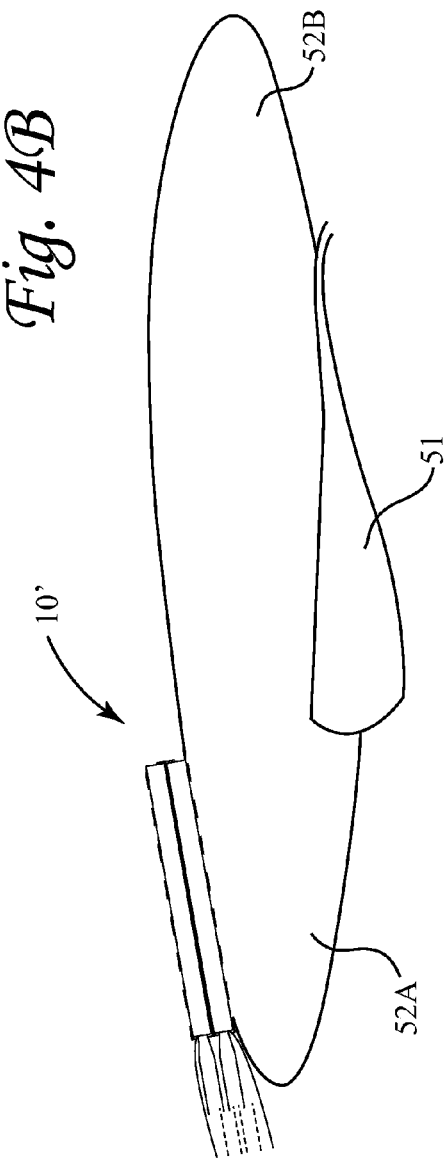

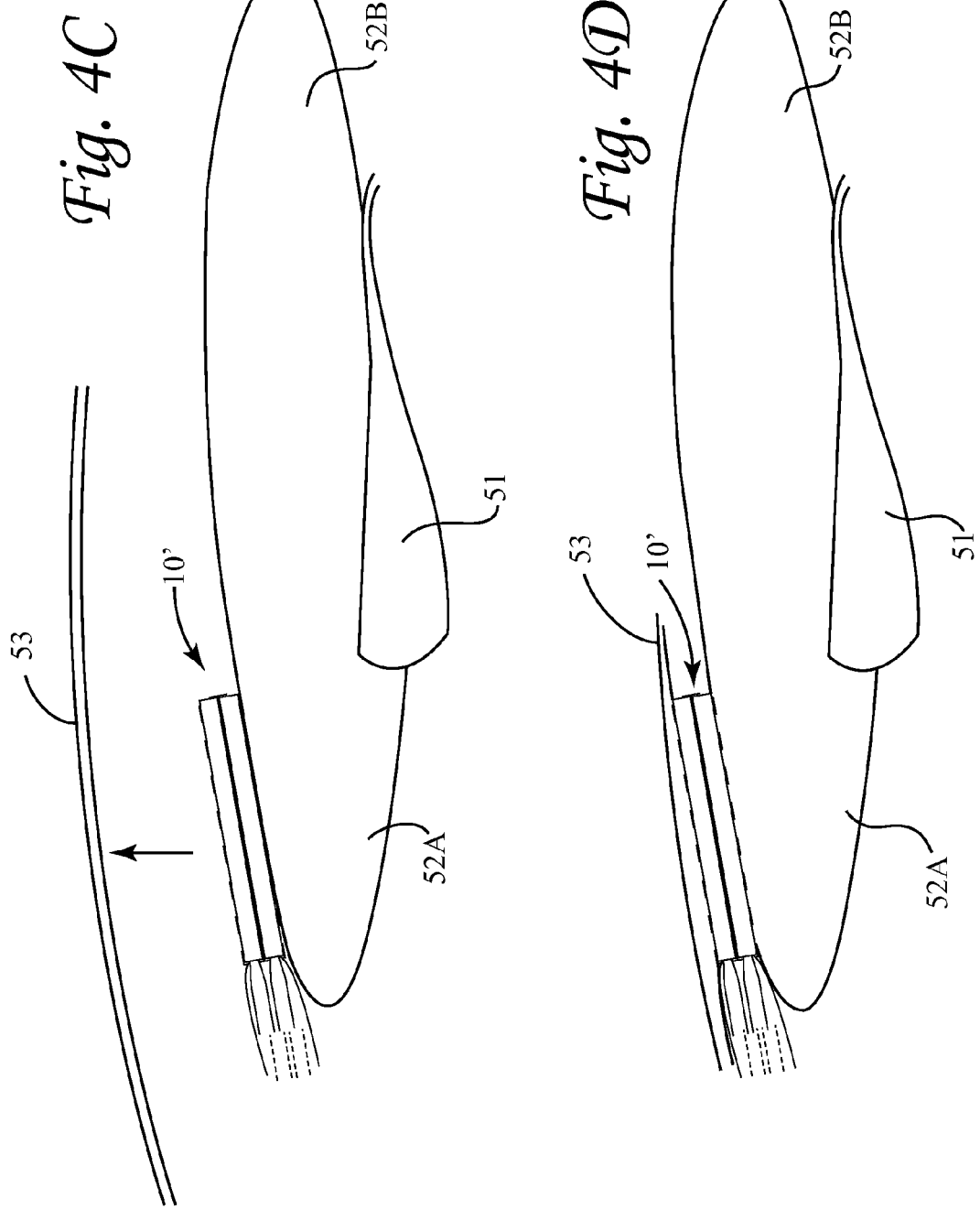

SUCTION-BASED TISSUE MANIPULATOR

BACKGROUND OF THE INVENTION

1. Field of the Invention

This invention relates to surgical instruments used to grasp, move and hold tissue during surgery.

2. State of the Art

As shown in FIG. 1, the human digestive system includes a biliary tract (gall bladder and bile ducts) that carries and stores bile that contains substances that allow fats to be emulsified. Bile also stimulates the secretion of an enzyme concerned with the breakdown of fats. Bile is secreted by the liver and stored in the gallbladder until needed. The gallbladder is a small pear-shaped organ. When fat is eaten, the gallbladder is stimulated to contract and bile stored in the gallbladder flows down the cystic duct, into the common bile duct and to the small intestine. As well as acting as a storage vessel, the gallbladder concentrates the bile within it by removing water through its wall.

The most common disorder of the biliary tract is gallstones. Why and how gallstones form is not fully understood, but it is thought that in some cases an abnormality in function causes the gallbladder to remove an excessive amount of water from the bile so that some of its constituents can no longer remain in solution. Gallstones occur very frequently in developed countries and may be associated with eating a diet that is high in fat and refined carbohydrates and low in fiber. Gallstones can give rise to various problems, including cholecystitis (inflammation of the gallbladder), choledocholithiasis (gallstones in the common bile duct), cholangitis (infection of the bile ducts), pancreatitis, and gallstone ileus (obstruction of the intestines by a gallstone). Other disorders of the biliary tract include biliary sludge and dysmotility (poor physiological function). Treatment of such disorders can involve laparoscopic gallbladder removal (laparoscopic cholecystectomy).

Laparoscopic cholecystectomy requires one or more small incisions in the abdomen to allow the insertion of laparoscopic surgical instruments and a small video camera into the abdominal cavity. After the initial incision(s), the abdominal cavity is inflated with gas (typically carbon dioxide) and the camera is positioned in the abdominal cavity. The camera sends a magnified image from inside the body to a video monitor, giving the surgeon a close-up view of the organs and tissues. The surgeon watches the video monitor and performs the operation by manipulating laparoscopic surgical instruments that extend into the abdominal cavity.

Typically, laparoscopic cholecystectomy is carried out by lifting the left lobe of the liver by manipulation of hook retractor to identify and clear Calot's Triangle (the area bound by the liver, cystic duct, and common hepatic duct). With the liver being held by the hook retractor, the gallbladder is grasped by non-crushing grasping mechanical forceps (e.g., Rotweiler forceps) and lifted up and away from the liver bed. With the liver held by the hook retractor and the gallbladder held by the forceps, the cystic duct is dissected free from the overlying tissue and the cystic duct and then clipped and cut. The cystic artery in then dissected, clipped and cut. The gallbladder is separated from the liver bed typically by a spatula-shaped instrument. The spatula design is ideal for conforming to the gallbladder bed and bluntly dissecting the gallbladder from the liver. Care is taken to not enter the gallbladder to prevent spillage of infected bile or gallstones. Any bleeding points seen on the liver bed are cauterized. With a small length of gallbladder remaining on the liver bed, the gallbladder is retracted towards the abdominal wall by the mechanical forceps to allow for visualization of the liver bed. The gallbladder is then completely removed from the liver bed and placed in a tissue retrieval bag (e.g., Endo-bag). The bag is closed and then removed from the abdominal cavity. Fluid irrigation and suction in the vicinity of the liver is performed typically until the fluid being returned is clear. All instruments are removed from the abdominal cavity, pressure is applied to the outside of the abdominal wall to express as much of the pneumoperitoneum (insufflation gas) as possible, and the incision site(s) are sutured closed.

As part of the laparoscopic cholecystectomy, the handle of the hook retractor that is used to lift and hold the liver remains in the working field of the surgeon(s) external to the abdomen and can interfere with hand movement of the surgeon(s) in this space. Moreover, to hold the liver in place, the hook retractor requires manual fixation by a surgeon (or mechanical fixation by a support structure disposed outside the abdominal cavity) that holds the retractor in place, thus increasing the complexity of the procedure.

Similar problems arise when using retractors and other instruments to manipulate other organs and tissue during laparoscopic and non-laparoscopic surgeries involving the abdominal cavity, such as surgeries involving the small intestine, large intestine, stomach, spleen, liver, pancreas, kidneys, and adrenal glands.

Moreover, similar problems arise when using retractors and other instruments to manipulate other organs and tissue during laparoscopic and non-laparoscopic surgeries involving the thoracic cavity or pelvic cavity, such as surgeries involving the heart, thoracic aorta, the pulmonary artery and all its branches, the superior and inferior vena cava, the pulmonary veins, the trachea, the bronchi and lungs, the esophagus, the endocrine glands, the thoracic duct, the reproductive organs, the urinary bladder, and the rectum.

Laparoscopic surgery as used herein means any surgery that involves one or more small incisions into a body cavity that allow for the insertion of laparoscopic surgical instruments and a small video camera into the body cavity. After the initial incision(s), the body cavity can be inflated with gas (typically carbon dioxide) and the camera is positioned in the body cavity. The camera sends a magnified image from inside the body to a video monitor, giving the surgeon a close-up view of the organs and tissues. The surgeon watches the video monitor and performs the operation by manipulating laparoscopic surgical instruments that extend into the body cavity. Laparoscopic surgery includes natural orifice translumenal endoscopic surgery (commonly referred to as "NOTES") where operations are performed with an endoscope passed through a natural orifice (mouth, urethra, anus, etc.) then through an internal incision into the stomach, vagina, bladder or colon into the desired body cavity (e.g., abdomen). NOTES is advantageous because it avoids external incisions and scarring associated therewith. Laparoscopic surgery also includes single port access (SPA) surgery, which is also known as single incision laparoscopic surgery (SILSTM) or one port umbilical surgery (OPUS) or natural orifice transumbilical surgery (NOTUS). SPA is a minimally invasive surgical procedure in which the surgeon operates almost exclusively through a single entry point, typically the patient's umbilicus.

Thus, there is a need for improved devices that can effectively grasp, retract and hold body organs and tissue during surgical procedures with minimal risk in rupturing and/or otherwise damaging such tissue.

SUMMARY OF THE INVENTION

It is therefore an object of the invention to provide a surgical assembly for lifting and manipulating tissue which reduces interference in the working field of the surgeon(s) adjacent the patient as compared to presently used systems.

It is another object of the invention to provide such a surgical assembly which effective grasps and holds tissue with minimal trauma to the tissue being grasped.

It is yet another object of the invention to provide such a surgical assembly which is simple and inexpensive relative to presently used systems.

It is a further object of the invention to such a surgical assembly which is suitable for minimally invasive laparoscopic surgery.

It is still another object of the invention to provide such a surgical assembly which a reduced number of parts that is simple and effective to use.

In accord with these objects, which will be discussed in detail below, a surgical assembly according to the invention broadly includes a flexible shell that defines a flexible sheet-like structure with a major top wall opposite a major bottom wall. The top wall is impermeable to air flow therethrough and has a first set of holes that allow for air flow therethrough. The bottom wall is impermeable to air flow therethrough and has a second set of holes that allow for air flow therethrough. A first fluid path supplies a source of suction to the first set of holes in a manner that is independent to suction supplied the second set of holes. A second fluid path supplies a source of suction to the second set of holes in a manner that is independent to suction supplied to the first set of holes. The supply of suction to the first set of holes is used to engage and hold tissue adjacent the top wall by suction forces applied through the first set of holes. The supply of suction to the second set of holes is used to engage and hold tissue adjacent the bottom wall by suction forces applied through the second set of holes. The tissue that is engaged adjacent the top wall is sealably disposed about the first set of holes, and tissue that is engaged adjacent the bottom wall is sealably disposed about the second set of holes.

In the preferred embodiment, the flexible shell includes walls that define internal top and bottom chambers that are disposed opposite one another. The top chamber is bounded by the top wall, and the bottom chamber is bounded by the bottom wall. The first fluid path is fluidly coupled to the top chamber, and the second fluid path is fluidly coupled to the bottom chamber. The top chamber preferably includes a first diffusion member that disperses vacuum flow across the first set of holes of the top wall, and the bottom chamber preferably includes a second diffusion member that disperses vacuum flow across the second set of holes of the bottom wall. The first and second diffusion members can also function to enhance structural integrity of the respective chamber and helps prevent the respective chamber from buckling or collapsing under vacuum loads applied thereto when engaging tissue.

The surgical assembly of the invention advantageously provides for lifting, manipulating and holding tissue without the need for manual fixation by a surgeon (or mechanical fixation by an external support structure disposed adjacent the patient). It also operates to reduce interference in the working field of the surgeon(s) adjacent the patient. It also provides effective tissue grasping with minimal tissue damage. It also accomplishes the objects of the invention with a minimum number of parts and may be used to replace expensive laparoscopic tissue grasping and manipulation instruments.

Additional objects and advantages of the invention will become apparent to those skilled in the art upon reference to the detailed description taken in conjunction with the provided figures.

BRIEF DESCRIPTION OF THE DRAWINGS

FIG. 3A is a cross-sectional schematic view of an alternate embodiment of a tissue grasper in accordance with the present invention.

FIG. 3B is a perspective view of the tissue grasper of FIG. 3A.

FIG. 3C is a schematic view of a surgical instrument employing the tissue grasper of FIGS. 3A and 3B.

FIGS. 4A-4D are pictorial illustrations that depict the use of the tissue grasper of FIGS. 3A-3B for grasping and holding a gallbladder during a surgical operation of the abdominal cavity, such as a cholecystectomy.

DETAILED DESCRIPTION OF THE PREFERRED EMBODIMENTS

Figure 1:
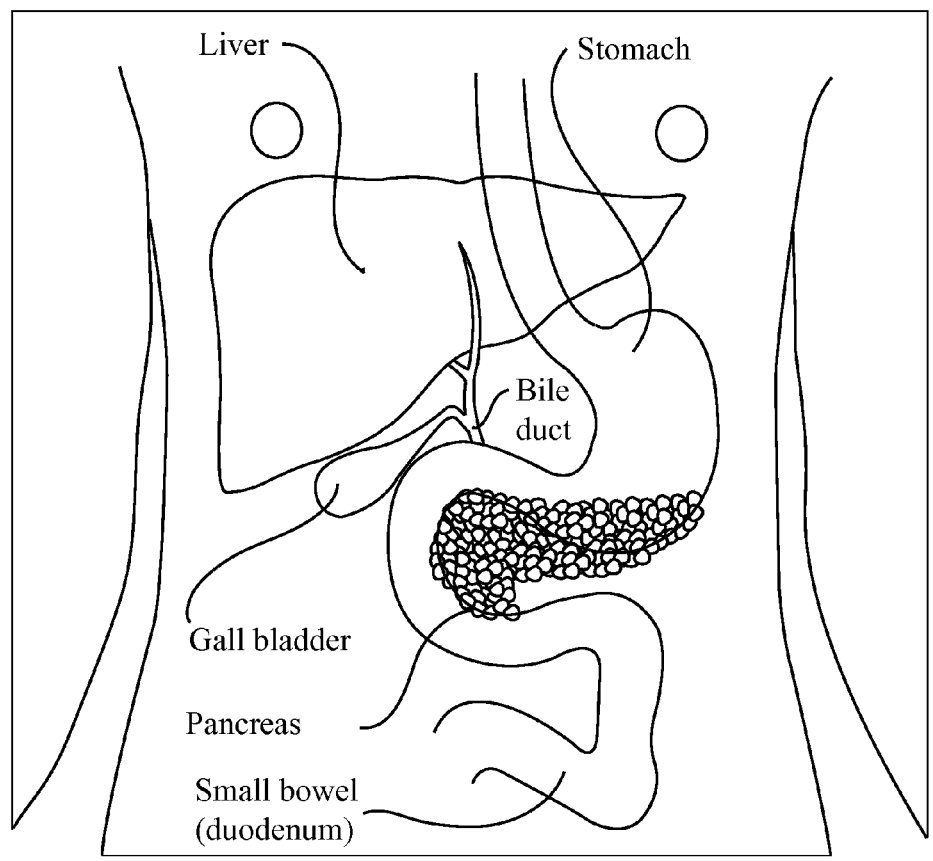
FIG. 1 is an illustration showing anatomic details of the abdominal cavity of the human body.
Figure 2A:
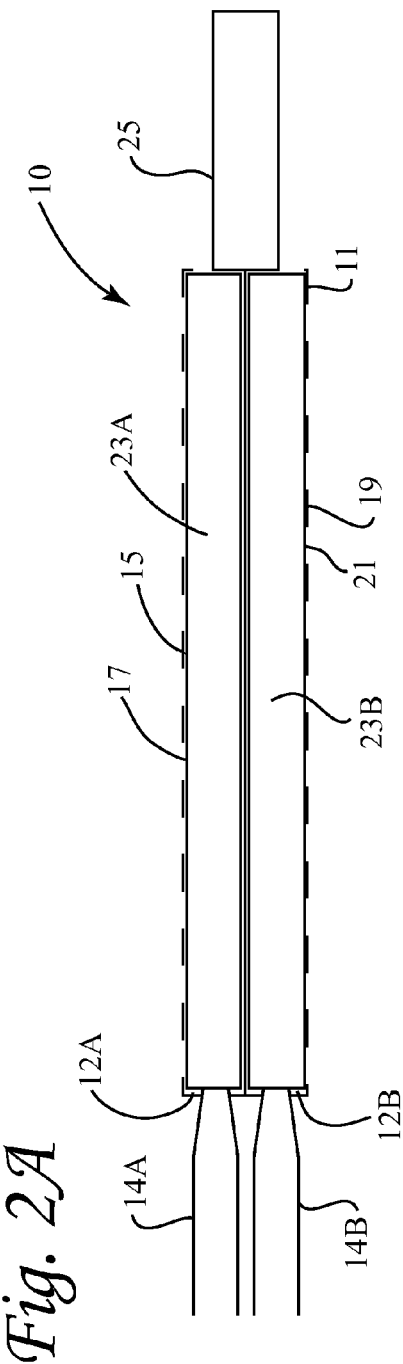
FIG. 2A is a cross-sectional schematic view of an exemplary embodiment of a tissue grasper in accordance with the present invention.
Figure 2B:
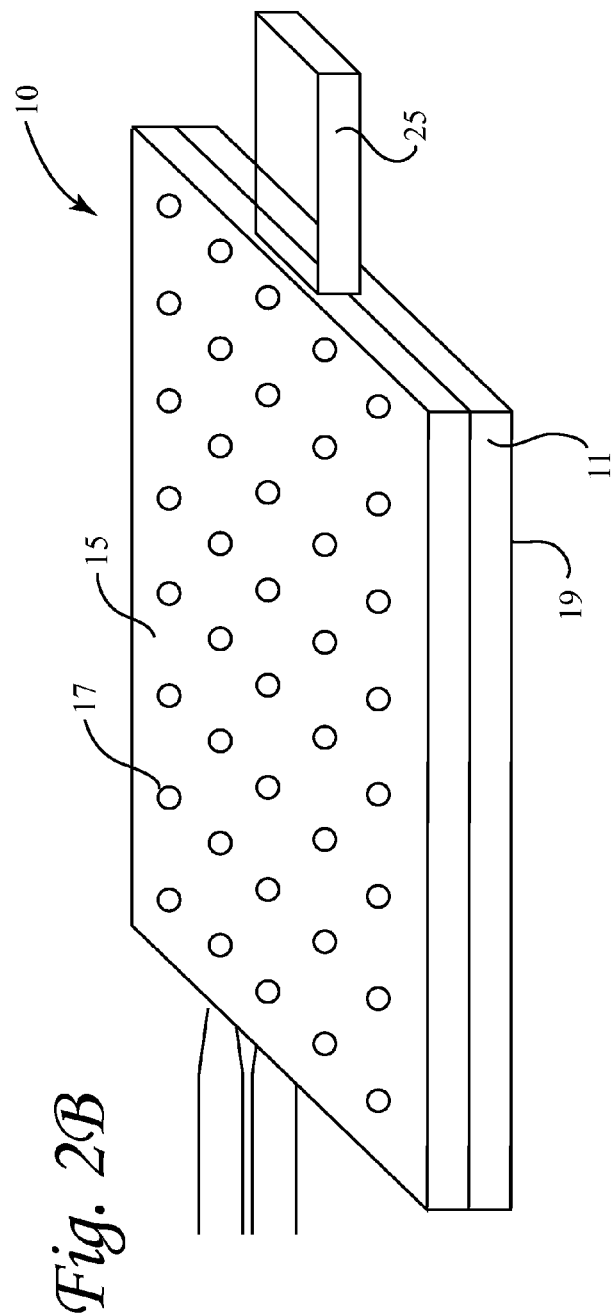
FIG. 2B is a perspective view of the tissue grasper of FIG. 2A.
Figure 2C:
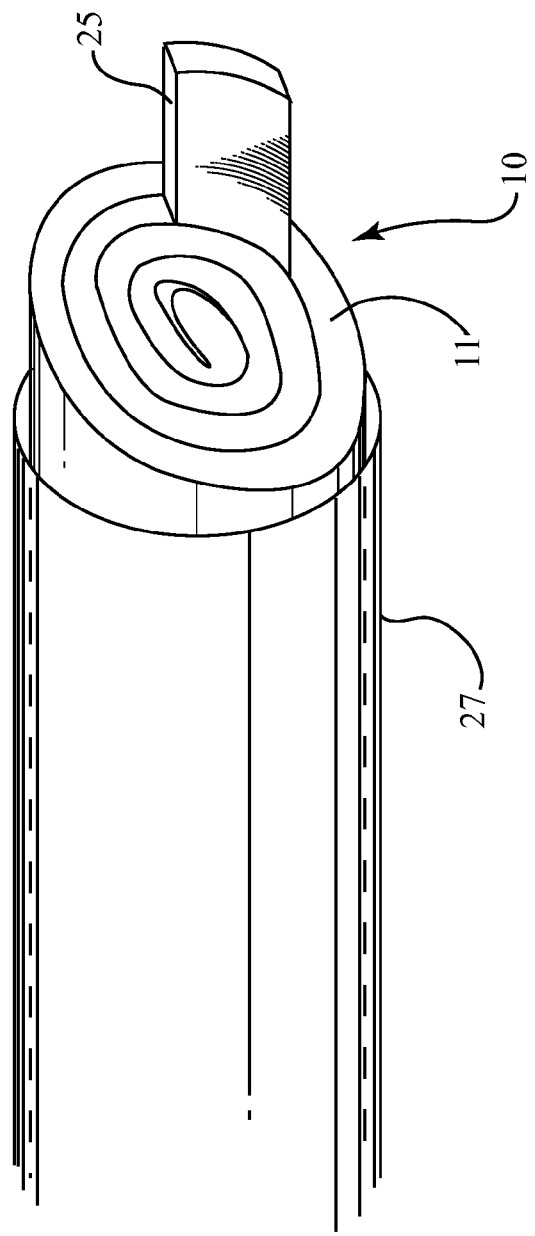
FIG. 2C is a pictorial illustration of a configuration of the tissue grasper of FIGS. 2A and 2B providing deployment from a cannula suitable for laparoscopic surgical applications.

Turning now to FIGS. 2A-2C, a surgical apparatus 10 in accordance with the present invention is provided for engaging and holding tissue during a surgical procedure. The apparatus 10 includes a flexible shell or skin 11 that defines a flexible sheet-like structure with internal top and bottom chambers 12A, 12B that are disposed opposite one another as best shown in FIG. 2A. A first flexible tube 14A is fluidly coupled to the top chamber 12A. A second flexible tube 14B is fluidly coupled to the bottom chamber 12B. The first tube 14A is fluidly coupled to a vacuum line (not shown) in a manner that provides for supply of suction (negative air pressure) to the first chamber 12A independent from the supply provided to the second chamber 12B. The second tube 14B is fluidly coupled to the same vacuum line (or another vacuum line) in a manner that provides for supply of suction (negative air pressure) to the second chamber 12B that is independent from the supply provided to the first chamber 12A. The tubes 14A and 14B can be joined or held together if desired. The tubes 14A, 14B can also be realized a multi-lumen conduit. The conduit(s) that realize the tubes 14A, 14B are preferably flexible in nature such that they can be moved in the working field of the surgeon(s) adjacent the patient in order to minimize obtrusiveness of the conduits from the hand movements of the surgeon(s). The walls of the top and bottom chambers 12A, 12B are realized from a flexible material that is generally impermeable to air flow therethrough, which is necessary to generate a pressure differential between the respective chambers and the ambient environment for suction purposes as described herein. In the preferred embodiment, the walls of the top and bottom chambers is realized from a medical-grade sealing elastomer, such as butyl and nitrile rubbers, silicones, perfluorocarbons (e.g., PTFE), polyurethanes, vinyls, as well as other medical-grade sealing elastomeric materials. Such sealing elastomers allow for conformance of the shell 12 to the tissue to allow for proper sealing therebetween, and also minimize any risk of puncture and other damage to the tissue that it contacts.

As shown in FIG. 2B, the major top wall 15 of the top chamber 12A has a pattern of holes 17 that allow for air flow into the top chamber 12A upon supply of suction to the top chamber 12A. Similarly, the major bottom wall 19 of the bottom chamber 12B has a pattern of holes 21 that allow for air flow into the bottom chamber 12B upon supply of suction to the bottom chamber 12B.

The top chamber 12A includes a diffusion member 23A (such as a layer of open cell foam) that disperses the vacuum flow across the pattern of holes 17 on the top wall 15. The diffusion member 23A also enhances the structural integrity of the top chamber 12A and helps prevent the top chamber 12A from buckling or collapsing under the vacuum load applied thereto. The bottom chamber 12B includes a diffusion member 23B (such as a layer of open cell foam) that disperses the vacuum flow across the pattern of holes 21 on the bottom wall 19. The diffusion member 23B also enhances the structural integrity of the bottom chamber 12B and helps prevent the bottom chamber 12B from buckling or collapsing under the vacuum load applied thereto.

In an alternative embodiment, the diffusion member 23A can be substituted by (or enhanced with the addition of) a supportive skeletal network that enhances structural integrity of the top chamber 12A and prevents the top chamber 12A from buckling or collapsing under vacuum loads applied thereto. Similarly, the diffusion member 23B can be substituted by (or enhanced with the addition of) a supportive skeletal network that enhances structural integrity of the bottom chamber 12B and prevents the bottom chamber 12B from buckling or collapsing under vacuum loads applied thereto. Such supportive skeletal networks can be realized by a wire or plastic mesh or other suitable support structure.

One or more tabs 25 (one shown) extend from the shell 11. The tab(s) 25 is grabbed by a grasping device, such as a laparoscopic forceps instrument, to position and move the shell 11 during use as desired.

It is contemplated that the color of the major top wall 15 of the top chamber 12A can be distinct relative to the color of the major bottom wall 19 of the bottom chamber 12B to allow for easy identification of the orientation of the shell 11 and proper control of negative air pressure to the respective chambers.

During use, the supply of suction to the bottom chamber 12B operates to engage and hold tissue adjacent the bottom wall 19 of the bottom chamber 12B by negative air pressure within the top chamber 12B (FIG. 4B). Such negative air pressure induces suction that extends through the holes 21 to retain and hold the tissue adjacent the bottom wall 19. Independently, the supply of suction to the top chamber 12A is used to engage and hold tissue adjacent the top wall 15 of the top chamber 12A by negative air pressure within the top chamber 12A. Such negative air pressure induces suction that extends through the holes 17 to retain and hold the tissue adjacent the top wall 15. Tissue that is engaged adjacent the bottom wall 19 is sealably disposed about the pattern of holes 21 in the bottom wall 19 with the pattern of holes 21 covering an area that is smaller than the area of tissue sealably disposed thereabout. Tissue that is engaged adjacent the top wall 15 is sealably disposed about the pattern of holes 17 in the top wall 15 with the pattern of holes 17 covering an area that is smaller than the area of tissue sealably disposed thereabout. Tissue that is engaged adjacent the top wall 15 is released from the top wall 15 by venting the first fluid path 14A, which removes the suction forces that are applied to the tissue through the holes 17 in the top wall 15. Tissue that is engaged adjacent the bottom wall 19 is released from the bottom wall 19 by venting the second fluid path 14B, which removes the suction forces that are applied to the tissue through the holes 21 in the bottom wall 19.

As shown in FIG. 2C, the flexible shell 11 can be rolled-up on itself and housed at the distal end of a flexible or rigid cannula 27. In the preferred embodiment, the cannula 27 has an outer diameter preferably in a range of 5-10 mm for insertion through a common laparoscopic port. With the distal end of the cannula 27 positioned inside a body cavity (e.g., an abdominal cavity during laparoscopic surgery therein), the flexible shell 11 (together with the tab 25) can be deployed from the distal end of the cannula 27 and into the body cavity, where it is unrolled for use in engaging and holding tissue inside the body cavity (FIGS. 4A-4D).

Turning now to FIGS. 3A-3C, an alternate embodiment of a surgical apparatus 10' in accordance with the present invention is provided for engaging and holding tissue during a surgical procedure. The apparatus 10' includes a flexible shell or skin 11' that defines a flexible sheet-like structure with internal top and bottom chambers 12A, 12B similar to the embodiment of FIGS. 2A-2C. A first flexible tube 14A is fluidly coupled to the top chamber 12A. A second flexible tube 14B is fluidly coupled to the bottom chamber 12B. The first tube 14A is fluidly coupled to a vacuum line (not shown) in a manner that provides for supply of suction (negative air pressure) to the first chamber 12A independent from the supply provided to the second chamber 12B. The second tube 14B is fluidly coupled to the same vacuum line (or another vacuum line) in a manner that provides for supply of suction (negative air pressure) to the second chamber 12B that is independent from the supply provided to the first chamber 12A. The walls of the top and bottom chambers 12A, 12B are realized from a flexible material that is generally impermeable to air flow therethrough, which is necessary to generate a pressure differential between the respective chambers and the ambient environment for suction purposes as described herein. In the preferred embodiment, the walls of the top and bottom chambers is realized from a medical-grade sealing elastomer, such as butyl and nitrile rubbers, silicones, perfluorocarbons (e.g., PTFE), polyurethanes, vinyls, as well as other medical-grade sealing elastomeric materials. Such sealing elastomers allow for conformance of the shell 12 to the tissue to allow for proper sealing therebetween, and also minimize any risk of puncture and other damage to the tissue that it contacts.

As shown in FIG. 3B, the major top wall 15 of the top chamber 12A has a pattern of holes 17 that allow for air flow into the top chamber 12A upon supply of suction to the top chamber 12A. Similarly, the major bottom wall 19 of the bottom chamber 12B has a pattern of holes 21 that allow for air flow into the bottom chamber 12B upon supply of suction to the bottom chamber 12B.

The top chamber 12A includes a diffusion member 23A (such as a layer of open cell foam) that disperses the vacuum flow across the pattern of holes 17 on the top wall 15. The diffusion member 23A also enhances the structural integrity of the top chamber 12A and helps prevent the top chamber 12A from buckling or collapsing under the vacuum load applied thereto. The diffusion member 23A can also aid in preventing tissue from being sucked through the holes 17 and any tissue damage that can result therefrom. The bottom chamber 12B includes a diffusion member 23B (such as a layer of open cell foam) that disperses the vacuum flow across the pattern of holes 21 on the bottom wall 19. The diffusion member 23B also enhances the structural integrity of the bottom chamber 12B and helps prevent the bottom chamber 12B from buckling or collapsing under the vacuum load applied thereto. The diffusion member 23B can also aid in preventing tissue from being sucked through the holes 21 and any tissue damage that can result therefrom.

In an alternative embodiment, the diffusion member 23A can be substituted by (or enhanced with the addition of) a supportive skeletal network that enhances structural integrity of the top chamber 12A and prevents the top chamber 12A from buckling or collapsing under vacuum loads applied thereto. Similarly, the diffusion member 23B can be substituted by (or enhanced with the addition of) a supportive skeletal network that enhances structural integrity of the bottom chamber 12B and prevents the bottom chamber 12B from buckling or collapsing under vacuum loads applied thereto. Such supportive skeletal networks can be realized by a wire or plastic mesh or other suitable support structure.

As best shown in FIG. 3C, a support member 29 is coupled to the shell 11' for positioning and moving the shell 11' as desired. In the preferred embodiment, the support member 29 is a cannula that houses the first and second fluid paths 14A, 14B therein. It is contemplated that the fluid paths 14A, 14B can be tubes that extend through the interior space of the support cannula 29. Alternatively, the fluid paths 14A, 14B can be realized by fluid passageways that are integrally formed (for example, by molding) as part of the support cannula 29. It is also contemplated that the fluid paths 14A, 14B can be defined by tubing supported on the exterior of the support member 29. The mechanical coupling between the support member 29 and the shell 11' can be realized by a coupling adapter (not shown) or other suitable mechanisms. The coupling can be bendable or otherwise moveable about one more axes to allow for flexible orientation of the shell 11' relative to the support member 29. The support member 29 can be bendable, hinged, shortened, a two-piece unit with detachable connectors or other configuration that minimizes obtrusiveness of the support member 29 in the working field of the surgeon(s) adjacent the patient.

It is contemplated that the color of the major top wall 15 of the top chamber 12A can be distinct relative to the color of the major bottom wall 19 of the bottom chamber 12B to allow for easy identification of the orientation of the shell 11' and proper control of negative air pressure to the respective chambers.

During use, the supply of suction to the bottom chamber 12B operates to engage and hold tissue adjacent the bottom wall 19 of the bottom chamber 12B by negative air pressure within the top chamber 12B (FIG. 4B). Such negative air pressure induces suction that extends through the holes 21 to retain and hold the tissue adjacent the bottom wall 19. Independently, the supply of suction to the top chamber 12A is used to engage and hold tissue adjacent the top wall 15 of the top chamber 12A by negative air pressure within the top chamber 12A. Such negative air pressure induces suction that extends through the holes 17 to retain and hold the tissue adjacent the top wall 15. Tissue that is engaged adjacent the bottom wall 19 is sealably disposed about the pattern of holes 21 in the bottom wall 19 with the pattern of holes 21 covering an area that is smaller than the area of tissue sealably disposed thereabout. Tissue that is engaged adjacent the top wall 15 is sealably disposed about the pattern of holes 17 in the top wall 15 with the pattern of holes 17 covering an area that is smaller than the area of tissue sealably disposed thereabout. Tissue that is engaged adjacent the top wall 15 is released from the top wall 15 by venting the first fluid path 14A, which removes the suction forces that are applied to the tissue through the holes 17 in the top wall 15. Tissue that is engaged adjacent the bottom wall 19 is released from the bottom wall 19 by venting the second fluid path 14B, which removes the suction forces that are applied to the tissue through the holes 21 in the bottom wall 19.

In the preferred embodiment, the proximal portion of the support member 29 is used as a handle to allow the operator to guide and position the distal end of the support member 29 and the flexible shell 11' secured thereto. The proximal portion of the support member 29 also includes first and second valves 31A, 31B as shown in FIG. 3C. The first valve 31A is fluidly coupled to the first fluid path 14A. During use, it is connected to a vacuum line (not shown) and is operated to control the supply of suction to the first fluid path 14A for engaging and holding tissue adjacent the top wall 15 of flexible shell 11'. The second valve 31B is fluidly coupled to the second fluid path 14B. During use, it is connected between to a vacuum line (not shown) and is operated to control the supply of suction to the second fluid path 14B for engaging and holding tissue adjacent the bottom wall 19 of flexible shell 11'. The first valve 31A is also operable to vent the first fluid path 14A to release tissue engaged and held by suction forces adjacent the top wall 15 of shell 11', and the second valve 31B is also operable to vent the second fluid path 14B to release tissue engaged and held by suction forces adjacent the bottom wall 19 of shell 11'.

Similar to the configuration shown in FIG. 2C, the flexible shell 11' can be rolled-up on itself and housed at the distal end of overtube 27'. In the preferred embodiment, the overtube 27' has an outer diameter preferably in a range of 5-10 mm for insertion through a common laparoscopic port. With the distal end of the cannula overtube 27' positioned inside a body cavity (e.g., an abdominal cavity during laparoscopic surgery therein), the flexible shell 11' can be deployed from the distal end of the overtube 27' (by moving the overtube 27' proximally to a position shown in FIG. 3C) and positioned in the body cavity, where it is unrolled for use in engaging and holding tissue inside the body cavity (FIGS. 4A-4D).

In use, a practitioner will select the apparatus 10' and deploy it within a body cavity, for example an abdominal cavity during laparoscopic gallbladder surgery as illustrated in FIGS. 4A-4D. For laparoscopic applications, the shell 11' can be initially deployed in the body cavity in a rolled-up configuration (FIG. 2C) and then unrolled inside the body cavity for use therein. The shell 11' is then positioned with the bottom wall 19 near or adjacent tissue to be engaged and held, such as the left lobe 52A of the liver for lifting the liver to access the gallbladder 51 adjacent the right lobe 52B of the liver as shown. Suction is supplied via the second fluid path 14B to produce negative air pressure that engages and holds the left liver lobe 52A adjacent the bottom wall 19 of the shell 11'. The shell 11' and left liver lobe 52A secured thereto by suction can then be moved. For example, it can be moved upward as shown in FIG. 4C until the top wall 15 of the shell 11' is adjacent or near the abdominal wall 53. Simultaneous to the application of suction that secures the left liver lobe 52A adjacent the bottom wall 19, suction is supplied via the first fluid path 14A to produce negative air pressure that engages and holds the abdominal wall 53 adjacent the top wall 15 of the shell 11' (with the left liver lobe 52A secured thereto by suction) as shown in FIG. 4D. In this manner, the shell 11' is used to retract the left liver lobe 42A towards the abdominal wall and secure it to the abdominal wall to allow for visualization of the liver bed. The gallbladder 51 can then be completely removed from the liver bed (if not done so already). The shell 11' and left liver lobe 52A secured thereto can be released from the abdominal wall 53 by venting the first fluid path 14A. And the left liver lobe 52A can be released from the bottom wall 19 of the shell 11' by venting the second fluid path 14B. Such operations can be used to release the left liver lobe from the shell 11' as desired. Similar operations can be carried out using the shell 11 of the embodiment of FIGS. 2A-2C.

Note that suction can be supplied by both the first and second fluid paths 14A, 14B together to grasp and hold tissue adjacent the top and bottom walls of the shell 11, or alone (singularly or alternatingly). For example, suction forces can be constantly supplied by one of the first and second fluid paths, while suction forces are applied and released by the other fluid path as needed.

Similar operations can be performed for grasping and holding organs and tissue during laparoscopic and non-laparoscopic surgeries involving the abdominal cavity (e.g., surgeries involving the small intestine, large intestine, stomach, spleen, liver, pancreas, kidneys, and adrenal glands). Examples of such surgeries include laparoscopic lap-band and other bariatric surgeries, laparoscopic NISSEN fundoplication, and laparoscopic colon surgery.

Moreover, similar operations can be performed for grasping and holding organs and tissue during laparoscopic and non-laparoscopic surgeries involving the thoracic cavity (e.g., surgeries involving the heart, thoracic aorta, the pulmonary artery and all its branches, the superior and inferior vena cava, the pulmonary veins, the trachea, the bronchi and lungs, the esophagus, the endocrine glands, and the thoracic duct), and for grasping and holding organs and tissue during surgeries involving the pelvic cavity (e.g., surgeries involving the reproductive organs, urinary bladder, and rectum).

It is also contemplated that the flexible shell can employ one ore more stabilizing members that aid in maintaining structural integrity of the flexible shell under suction loading during use. For example, stabilizing members suitable for laparoscopic applications are described in U.S. Pat. Nos. 5,245,987; 5,271,385; 5,199,419; 5,195,506; and 5,195,505; which are herein incorporated by reference in their entireties.

Advantageously, the surgical assembly of the invention provides for lifting, manipulating and holding tissue without the need for manual fixation by a surgeon (or mechanical fixation by an external support structure disposed adjacent the patient). It also operates to reduce interference in the working field of the surgeon(s) adjacent the patient. It also provides effective tissue grasping with minimal tissue damage. It also accomplishes the objects of the invention with a minimum number of parts and may be used to replace expensive laparoscopic tissue grasping and manipulation instruments.

There have been described and illustrated herein several embodiments of a surgical assembly for grasping and holding tissue and methods for the use thereof. While particular embodiments of the invention have been described, it is not intended that the invention be limited thereto, as it is intended that the invention be as broad in scope as the art will allow and that the specification be read likewise. Thus, while particular materials for making the assembly have been disclosed, it will be appreciated that other materials may be used as well, and while exemplary diameters for the surgical instruments have been disclosed, other diameters can be utilized. In addition, while particular valving elements and fixation systems have been disclosed for controlling suction and positioning of the assembly, it will be understood that other mechanisms can be used. Moreover, while particular configurations of surgical instruments have been disclosed, it will be appreciated that other configurations could be used as well. It will therefore be appreciated by those skilled in the art that yet other modifications could be made to the provided invention without deviating from its spirit and scope as claimed.

What is claimed is:

1. An apparatus for grasping and holding tissue comprising:
   a flexible sheet with walls that define internal top and bottom chambers that adjoin one another and that are moved together as a unitary part during use, the walls including a major top wall opposite a major bottom wall that are both adapted to conform to tissue during use, the top wall constructed of a material impermeable to air flow therethrough and having a first set of holes that allow for air flow therethrough, and the bottom wall constructed of a material impermeable to air flow therethrough and having a second set of holes that allow for air flow therethrough; and
   a first fluid path supplying a source of suction to the top chamber and the first set of holes in a manner that is independent to suction supplied the bottom chamber and the second set of holes, and a second fluid path supplying a source of suction to the bottom chamber and the second set of holes in a manner that is independent to suction supplied to the top chamber and the first set of holes;
   wherein the supply of suction to the top chamber and the first set of holes is used to engage and hold tissue adjacent the top wall by suction forces applied through the first set of holes, and the supply of suction to the bottom chamber and the second set of holes is used to engage and hold tissue adjacent the bottom wall by suction forces applied through the second set of holes.

2. An apparatus according to claim 1, wherein:
   the top chamber is bounded by the top wall and the bottom chamber is bounded by the bottom wall.

3. An apparatus according to claim 2, wherein:
   the top chamber includes a first diffusion member that disperses vacuum flow across the first set of holes of the top wall, and the bottom chamber includes a second diffusion member that disperses vacuum flow across the second set of holes of the bottom wall.

4. An apparatus according to claim 3, wherein:
   the first and second diffusion members each comprise a layer of open cell foam.

5. An apparatus according to claim 3, wherein:
   the first and second diffusion members each enhance structural integrity of the respective chamber and helps prevent the respective chamber from buckling or collapsing under vacuum loads applied thereto when engaging tissue.

6. An apparatus according to claim 2, wherein:
   the walls that define the top chamber and the bottom chamber are constructed of an elastomeric material impermeable to air flow therethrough, wherein the elastomeric material provides flexibility that allows the sheet to conform to tissue.

7. An apparatus according to claim 2, wherein:
   the first fluid path is fluidly coupled to the top chamber, and the second fluid path is fluidly coupled to the bottom chamber.

8. An apparatus according to claim 1, wherein:
   tissue that is engaged adjacent the top wall is sealably disposed about the first set of holes, and tissue that is engaged adjacent the bottom wall is sealably disposed about the second set of holes.

9. An apparatus according to claim 8, wherein:
   the first set of holes cover an area that is smaller than the area of tissue sealably disposed about the first set of holes, and the second set of holes cover an area that is smaller than the area of tissue sealably disposed about the second set of holes.

10. An apparatus according to claim 1, further comprising:
a support member coupled to the sheet for positioning and moving the sheet as desired.

11. An apparatus according to claim 10, wherein:
the support member is a cannula that houses the first and second fluid paths.

12. An apparatus according to claim 1, wherein:
the flexible sheet has a rolled-up configuration where it is rolled up on itself and an expanded configuration where it takes a generally planar form.

13. An apparatus according to claim 12, further comprising:
a support member and a cannula;
wherein the sheet is supported by the support member coupled thereto for positioning and moving the sheet as desired; and
wherein the cannula stores the sheet in its rolled-up configuration for deployment therefrom and is an overtube that surrounds the support member.

14. An apparatus according to claim 1, further comprising:
at least one tab that extends from the sheet for grasping by an external device for positioning and moving the sheet as desired.

15. An apparatus according to claim 1, wherein:
the flexible sheet has a thickness that is substantially smaller than respective maximal width of said major top wall and said major bottom wall.

16. An apparatus according to claim 1, wherein:
the walls of the flexible shell are constructed of an elastomeric polymer material.

17. An apparatus according to claim 1, wherein:
the major top wall and the major bottom wall are adapted to allow for suction to be applied independently through two opposing faces of the sheet during use.

\* \* \* \* \*